(12) United States Patent
Pozzoli et al.

(10) Patent No.: US 9,109,000 B2
(45) Date of Patent: Aug. 18, 2015

(54) SYNTHESIS OF NUCLEOSIDES

(71) Applicant: FARMABIOS S.p.A., Gropello Cairoli (PV) (IT)

(72) Inventors: Claudio Gianluca Pozzoli, Monza (IT); Valentina Canevari, Rozzano (IT); Marco Brusasca, Valenza (IT); Lorenzo Menna, Milan (IT); Matteo Curti, Giussago (IT)

(73) Assignee: FARMABIOS, S.p.A., Gropello Cairoli (PV) (IT)

( * ) Notice: Subject to any disclaimer, the term of this patent is extended or adjusted under 35 U.S.C. 154(b) by 21 days.

(21) Appl. No.: 14/063,307

(22) Filed: Oct. 25, 2013

(65) Prior Publication Data

US 2014/0135490 A1  May 15, 2014

(30) Foreign Application Priority Data

Nov. 9, 2012 (IT) .............. MI2012A1918

(51) Int. Cl.
*C07H 19/00* (2006.01)
*C07H 19/12* (2006.01)
*C07F 7/22* (2006.01)

(52) U.S. Cl.
CPC .............. *C07H 19/12* (2013.01); *C07F 7/2284* (2013.01)

(58) Field of Classification Search
CPC .................................. C07F 7/22; C07H 19/12
See application file for complete search history.

(56) References Cited

U.S. PATENT DOCUMENTS 4,303,591 A    12/1981 Chou et al.

FOREIGN PATENT DOCUMENTS

EP    2 371 825 A1    10/2011

OTHER PUBLICATIONS

Italian Search Report dated Mar. 6, 2013, and Written Opinion.
Horst G. Langer; "Redistribution Reactions With Group IV Metal Compounds in Dimethylsulfoxide (DMSO)"; Tetrahedron Letters; vol. 8, No. 1, Jan. 1, 1967.

*Primary Examiner* — Lawrence E Crane
(74) *Attorney, Agent, or Firm* — Lucas & Mercanti, LLP

(57) ABSTRACT

A process for the preparation of nucleosides, derivatives and analogues thereof by coupling reaction of a protected suitable nitrogeneous purine or pyrimidine base, a derivative or analogue thereof and a protected suitable sugar in the presence of $SnCl_4$ comprising the removal of SnCl4 by adding DMSO directly into the reaction mixture is described. Preferably said process is used for the preparation of antiviral and antitumor agents having a nucleoside or nucleoside-like structure, still more preferably for the preparation of azacytidine, decitabine, chlorfarabine, cladribine, mizoribine. A residual tin content lower than 300 ppm is obtained with said process.

10 Claims, No Drawings

SYNTHESIS OF NUCLEOSIDES

CROSS-REFERENCE TO RELATED APPLICATION

This application claims the benefit of Italian Patent Application No. MI2012A001918,filed Nov. 9, 2012, the contents of which are incorporated herein by reference.

FIELD OF THE INVENTION

The present invention relates to a process for the preparation of nucleosides, derivatives and analogues thereof and, more particularly, relates to a process for the preparation of antiviral agents and antitumor agents having a nucleoside or nucleoside-like structure. Nucleosides are glycosylamines formed by a nitrogenous base linked to a ribose or deoxyribose sugar by a beta-glycosidic bond. Specific examples of nucleosides are cytidine, uridine, adenosine, guanosine, timidine and inosine.

BACKGROUND OF THE INVENTION

In medicine several nucleoside derivatives and analogous, that is compounds having a structure similar to nucleosides but differing from nucleosides for a specific component such as for example one or more atoms, functional groups or substructures, are used as antiviral or antitumor agents. The high capability of these nucleoside derivatives and analogues to cross the cell membrane and to be converted into nucleoside within the cell makes such compounds very interesting for the research.

Specific examples of nucleoside analogous of pharmacological interest are azacytidine, decitabine, chlofarabine, cladribine, mizoribine.

Particularly azacytidine and decitabine are compounds of high interest in chemotherapy and in the treatment of diseases such as myelodysplasic syndrome.

Nucleosides and analogues thereof are typically synthetized by coupling an optionally protected purine or pyrimidine base, a derivative or an analogue thereof, with a ribose or deoxyribose derivative having an electrophilic center at the anomeric carbon.

A known example pyrimidine base analogue is 5-azacytosine.

Three types of synthesis of nucleosides, derivatives and analogues thereof are practically known in the prior art:
  fusion method, which consists in heating the base and the sugar protected as acetyl at 155° C.
  metal salt method, which consists in reacting a metal salt of the base with a halogenated derivative of the protected sugar
  Hilbert-Johnson or Vorbruggen reaction (*J. Org. Chem.*, Vol. 39, No. 25, 1974, 3672-3674), which consists in reacting the silylated base with the protected sugar having an acetyl group on the anomeric hydroxyl group, in the presence of a Lewis acid.

U.S. Pat. No. 3,817,980 (Vorbruggen) describes a process for preparing 5-azapyrimidin-nucleoside derivatives by reaction of 2,4-bis-O-alkyl and 2,4-bis-O-silyl 5-azapyrimidine derivatives with a protected sugar derivative in the presence of a Lewis acid such as for example $SnCl_4$, $TiCl_4$, $ZnCl_2$, $BF_3OEt_2$. The resultant azapyrimidin-nucleosides can be converted into the corresponding free nucleosides by simple saponification.

The process described by Vorbruggen shows some drawbacks due to the use of metal Lewis acids, particularly $SnCl_4$, for the 5-azacytidine synthesis:
  the nucleosides obtained by the coupling reaction contain a high amount of metals, particularly tin, difficult to remove;
  during the aqueous work-up of the coupling reaction emulsions and colloids are formed slowing the phase separation. Then 5-azacytidine, which is unstable in water, remains for a long time in contact with an aqueous solution giving degradation products.

For the above reasons, the process described by Vorbruggen is not suitable for the large-scale production of 5-azacytidine.

SUMMARY OF THE INVENTION

To overcome the drawbacks due to the use of $SnCl_4$ in the synthetic process of nucleosides, analogues and derivatives thereof, particularly 5-azacytidine, other synthetic methods using different coupling agents and catalysts have been developed. U.S. Pat. No. 4,082,911 (Vorbruggen) describes a process for preparing nucleosides by catalytic reaction of a 1-O-acyl, a 1-O-alkyl or a 1-halogen derivative of a protected sugar with a silylated nucleoside base. The used catalyst is a trialkyl silyl ester of an esterificable mineral acid or of a strong organic acid, such as for example trimethylsilyl esters of perchloric, fluorosulfonic or trifluoromethansulfonic acid. This process, avoiding the use of Lewis acid, allows to avoid the formation of colloids and emulsions.

U.S. Pat. No. 8,058,424, 7,038,038, 7,858,774 and 2012/0029181 (Ionescu) describe processes for the preparation of 5-azacytidine by a coupling reaction between silylated 5-azacytosine and a protected derivative of β-D-ribofuranose in the presence of trimethylsilyl trifluoromethansulfonate.

EP 2 371 825 (De Ferra) describes a process for the synthesis of azacytidine and decitabine comprising the silylation reaction of azacytosine with N,O-bis-trimethylsilyl-trifluoroacetamide at low temperatures followed by the coupling reaction between the silylated azacytosine and the protected sugar directly in the silylation reaction mixture without isolating the protected azacytosine. The deprotection of azacytidine is carried out by adding a basic agent to the coupling reaction mixture after the replacement of the solvent used in the coupling with a suitable solvent for the deprotection reaction.

These processes, even avoiding the use of metal Lewis acids, particularly $SnCl_4$, and the drawbacks connected with it, require the use of catalysts more expensive and less available than the Lewis acid used in the conventional processes.

There is still the need of a process for the synthesis of nucleosides, derivatives and analogues thereof by coupling reaction in the presence of metal Lewis acids, particularly $SnCl_4$, allowing the easy removal of the metal residues from the reaction product and making easier the work-up of the coupling reaction.

Some processes for the removal of $SnCl_4$ from the waste waters of reactions using $SnCl_4$ as catalyst are known in the art.

U.S. Pat. No. 4,303,591 (Chou) describes a process for removing $SnCl_4$ from waste streams, particularly from waste streams of reactions leading to the formation of cephalosporins through a mechanism of opening and closure of the penicillin ring catalyzed by stannic chloride. Cephalosporins are isolated by filtration leaving $SnCl_4$ dissolved in the waste streams. The catalyst is recovered by precipitating the corresponding complex $SnCl_4$-DMSO by adding DMSO to the reaction wastes.

The process described by Chou requires that the waste streams are free of suspended solids before adding DMSO to have an optimum precipitation of the $SnCl_4$-DMSO complex.

The application of the process described by Chou in the process for the synthesis of nucleosides, derivatives and analogues thereof by coupling reaction in the presence of stannic chloride does not overcome the above reported drawbacks because the isolation of the reaction products before removing stannic chloride should be needed so incurring in the formation of emulsions and colloids.

We have now found that the $SnCl_4$ present in the coupling reaction mixture for the preparation of nucleosides, derivatives and analogues thereof can be removed by adding DMSO directly in the coupling reaction mixture.

This process allows to remove most of the content of $SnCl_4$ used for the coupling reaction, directly from the reaction mixture containing also the nucleosides, derivatives or analogues thereof.

Preferably said process is useful for the preparation of antiviral and antitumor agents having a nucleoside or nucleoside-like structure, still more preferably for the preparation of azacytidine, decitabine, chlorfarabine, cladrabine, mizoribine.

After a simple work-up, an active ingredient with a residual tin content lower than 300 ppm, preferably lower than 200 ppm, can be obtained.

DETAILED DESCRIPTION OF THE INVENTION

Therefore, object of the present invention is a process for preparing nucleosides, derivatives or analogues thereof by coupling reaction between a suitable protected purine or pyrimidine nitrogenous base, a derivative or an analogue thereof in the presence of $SnCl_4$ characterized in that $SnCl_4$ is removed from the reaction mixture by adding DMSO directly to the reaction mixture and subsequently filtering the resultant $SnCl_4$-DMSO complex.

Preferably 2-4 eq DMSO with respect to tin are used in the process object of the present invention.

Preferably DMSO is added at a temperature of from 0° C. to 20° C., still more preferably of from 0° C. to 10° C.

The process object of the present invention is preferably used for preparing nucleosides, derivatives and analogues thereof such as azacytidine, decitabine, clofarabine, cladrabine, mizoribine, still more preferably azacitidine and decitabine.

The process object of the present invention is carried out by adding DMSO to the reaction mixture. Said reaction mixture can contain any organic solvent or mixture of organic solvents suitable for the coupling reaction between a protected suitable purine or pyrimidine nitrogenous base, a derivative or analogue thereof and a protected suitable sugar in the presence of $SnCl_4$, such as for example methylene chloride, chloroform, ethylene chloride, acetone, dioxane, tetrahydrofuran, dimethylformamide, benzene, toluene, carbon disulfide, carbon tetrachloride, tetrachloroethane, chlorobenzene, acetonitrile and ethylacetate or mixture thereof, preferably methylene chloride.

The removal of tin chloride from the reaction media is followed by the deprotection of the nucleoside, its derivative or analogue resultant from the coupling reaction between a protected suitable purine or pyrimidine nitrogenous base, a derivative or analogue thereof and a protected suitable sugar in the presence of $SnCl_4$, according to methods known in the art which foresee for example the treatment of the resultant residue with a base such as sodium methoxide. The resultant nucleoside, or derivative or analogue thereof, shows a purity >95%, preferably >97%.

The nucleoside, or derivative or analogue thereof, obtained according to the process object of the present invention can be further purified by crystallization according to known methods.

A preferred object of the present invention is a process for the preparation of nucleosides, or derivative or analogues thereof, obtained by the coupling reaction between a protected suitable purine or pyrimidine nitrogenous base, a derivative or analogue thereof and a protected suitable sugar in the presence of $SnCl_4$, characterized in that $SnCl_4$ is removed from the reaction media by adding DMSO directly to the reaction mixture and subsequent filtering the resultant $SnCl_4$-DMSO complex and in that the nucleosides, derivatives or analogues thereof, are crystallized from a mixture of DMSO and methanol.

Preferably, a small amount of base, preferably sodium methoxide, is added to the mixture of DMSO and methanol to complete the hydrolysis of mono- and di-acetates eventually present in the crude of the coupling reaction.

The amount of base which is added depends from the amount of mono- and di-acetates present in the reaction mixture. Also the choice of the base to be used depends from the conditions under which the process for the preparation of the nucleosides, derivatives or analogues thereof, is carried out. Preferably the same base of the deprotection reaction is used.

Generally, 0.002-0.008 equivalents of base with respect to the non protected suitable purine or pyrimidine nitrogenous base are added.

Preferably the crystallization is carried out in a mixture DMSO/methanol 1:3 by weight in the presence of 0.002-0.008 equivalents of sodium methoxide with respect to the non protected suitable purine or pyrimidine nitrogenous base used.

The process object of the present invention is particularly useful for the preparation of azacytidine form I.

The process object of the present invention shows several advantages among which the possibility to be carried out under anhydrous conditions by simple filtering, to remove 95-97% of the used tin, to avoid or decrease the emulsion formation, to separate the $SnCl_4$-DMSO complex from the reaction mixture without removing or separating the desired reaction products.

The addition of DMSO directly into the reaction mixture and the subsequent filtration of the resultant $SnCl_4$-DMSO complex allows to obtain an almost complete reduction of the tin content in the reaction mixture, an easier work-up because of the diminished occurrence of emulsions, a shorter contact time of the nucleosides, derivatives and analogues thereof with water.

The resultant nucleosides, derivatives and analogues thereof have a tin content lower than 300 ppm, preferably lower than 200 ppm, which is compatible with the injectable formulations of such compounds.

In a preferred embodiment of the process object of the present invention, a 5-azacytosine silyl derivative is dissolved in methylene chloride and a suitably protected O-acetyl-ribofuranose and $SnCl_4$ are added. The reaction mixture is kept under stirring for an hour. When the reaction is completed, the reaction mixture is cooled to a temperature of from 0° C. to 20° C. and DMSO is added. The precipitated $SnCl_4$-DMSO complex is recovered by filtration and the mother liquor containing azacytidine is concentrated up to a viscous residue to which methanol is added. Sodium methoxide in methanol is added to the resultant solution and the mixture is kept under stirring for 12 hours at room temperature. The precipitated solid is collected by filtering, washing with methanol and drying to give azacytidine with a tin content lower than 300 ppm.

In order to better illustrate the present invention without limiting it, the following examples are now given.

EXAMPLE 1

Preparation of Azacytidine

To a trimethylsilyl derivative of 5-azacytosine (18.5 g) dissolved in methylene chloride (500 mL) 1,2,3,5-tetra-O-acetyl-β-D-ribofuranose (1.0 eq) and $SnCl_4$ (1.2 eq) were added. The reaction mixture was kept under stirring for 1 hour. At the end of the reaction, the mixture was cooled up to a temperature of from 0° C. to 20° C. and DMSO (4 eq) was slowly added. The precipitated $SnCl_4$-DMSO complex was isolated by filtration. The mother liquor were concentrated under low pressure and methanol (100 mL) was added to the resultant oil residue. The residue was concentrated again under low pressure up to a viscous residue to which methanol (800 mL) was added and a 30% solution of sodium methoxide in methanol (0.2 eq) was added to the resultant solution. The solution was kept under stirring at room temperature for 12 hours and the resultant solid was filtered, washed with methanol (30 mL) and dried. 4.5 g azacytidine with a tin content lower than 200 ppm and a purity of 98.5% (determined by HPLC) was obtained.

EXAMPLE 2

Preparation of Aazacytidine

To a trimethylsilyl derivative of 5-azacytosine (18.5 g) dissolved in methylene chloride (500 mL) β-D-ribofuranose-1-acetate-2,3,5-tribenzoate (1.0 eq) and $SnCl_4$ (1.2 eq) were added. The reaction mixture was kept under stirring for 1 hour. At the end of the reaction, the mixture was cooled up to a temperature of from 0° C. to 20° C. and DMSO (4 eq) was slowly added. The precipitated $SnCl_4$-DMSO complex was isolated by filtration. The mother liquor were concentrated under low pressure and methanol (100 mL) was added to the resultant oil residue. The residue was concentrated again under low pressure up to a viscous residue to which methanol (800 mL) was added and a 30% solution of sodium methoxide in methanol (0.2 eq) was added to the resultant solution. The solution was kept under stirring at room temperature for 12 hours and the resultant solid was filtered, washed with methanol (30 mL) and dried. 5.3 g azacytidine with a tin content lower than 200 ppm and a purity of 97.3% (determined by HPLC) was obtained.

EXAMPLE 3

Preparation of Azacytidine

To a trimethylsilyl derivative of 5-azacytosine (40 g) dissolved in methylene chloride (400mL) 1,2,3,5-tetra-O-acetyl-β-D-ribofuranose (1.0 eq) were added and the solution was brought to a temperature of from 0° C. to 10° C. $SnCl_4$ (1.2 eq) was added to the solution and the temperature was left raise up to the room value. At the end of the reaction, the mixture was cooled up to a temperature of from 0° C. to 20° C. and DMSO (4 eq) was slowly added. The precipitated $SnCl_4$-DMSO complex was isolated by filtration. Sodium bicarbonate (4 eq) was added to the organic phase and the mixture was kept under stirring for 1 hour and the solid removed by filtration. The organic phase was washed with water (500 mL). The organic phases were separated, dried over sodium sulfate and concentrated under low pressure up to a viscous residue. The residue was added with methanol (300 mL) and a 30% solution of sodium methoxide in methanol (0.2 eq) was added to the resultant solution. The solution was kept under stirring at room temperature for 12 hours and the resultant solid was filtered, washed with methanol (30 mL) and dried. 10.3 g azacytidine with a tin content lower than 200 ppm and a purity of 98.7% (determined by HPLC) was obtained. The resultant azacytidine was crystallized from DMSO-methanol (34 mL DMSO/166 mL methanol) in the presence of 30% sodium methoxide in methanol (70 μL) to give a purity of 99.5% (determined by HPLC) and a tin content lower than 200 ppm.

EXAMPLE 4

Preparation of Azacytidine

To a trimethylsilyl derivative of 5-azacytosine (85 g) dissolved in methylene chloride (750 mL) 1,2,3,5-tetra-O-acetyl-β-D-ribofuranose (1.0 eq) were added and the solution was brought to a temperature of from 0° C. to 10° C. $SnCl_4$ (1.2 eq) was added to the solution and the temperature was left raise up to the room value. At the end of the reaction, the mixture was cooled up to a temperature of from 0° C. to 20° C. and DMSO (2 eq) was slowly added. The precipitated $SnCl_4$-DMSO complex was isolated by filtration. The organic phase was washed with a sodium bicarbonate saturated solution (300 mL) and the organic phases were separated, dried over sodium sulfate and concentrated under low pressure up to a viscous residue. The residue was added with methanol (1500 mL) and a 30% solution of sodium methoxide in methanol (0.4 eq) was added to the resultant solution. The solution was kept under stirring at room temperature for 12 hours and the resultant solid was filtered, washed with methanol (200 mL) and dried. The resultant product was crystallized from DMSO-methanol to give 18.6 g of azacytidine with a purity of 99.7% (determined by HPLC) and a tin content lower than 200 ppm.

EXAMPLE 5

Preparation of Azacytidine

To a trimethylsilyl derivative of 5-azacytosine (50 g) dissolved in methylene chloride (350 mL), β-D-ribofuranose-1-acetate-2,3,5-tribenzoate (1.0 eq) were added and the solution was brought to a temperature of from 0° C. to 10° C. $SnCl_4$ (1.2 eq) in methylene chloride (50 mL) was added to the solution and the temperature was left raise up to the room value. At the end of the reaction, the mixture was cooled up to a temperature of from 0° C. to 20° C. and DMSO (2 eq) was slowly added. The precipitated $SnCl_4$-DMSO complex was isolated by filtration. The organic phase was washed with a sodium bicarbonate saturated solution (100 mL) and the organic phases were separated, dried over sodium sulfate and concentrated under low pressure up to a viscous residue. The residue was added with methanol (1000 mL) and a 30% solution of sodium methoxide in methanol (0.4 eq) was added to the resultant solution. The solution was kept under stirring at room temperature for 12 hours and the resultant solid was filtered, washed with methanol (200 mL) and dried. 8 g of azacytidine with a purity of 98.3% (determined by HPLC) and a tin content lower than 200 ppm was obtained.

EXAMPLE 6

Preparation of Azacytidine

To a trimethylsilyl derivative of 5-azacytosine (85 g) dissolved in ethyl acetate (750 mL) 1,2,3,5-tetra-O-acetyl-β-D-ribofuranose (1.0 eq) were added and the solution was brought to a temperature of from 0° C. to 10° C. A solution of $SnCl_4$ (1.2 eq) in methylene chloride (100 mL) was added to the solution and the temperature was left raise up to the room value. At the end of the reaction, the mixture was cooled up to a temperature of from 0° C. to 20° C. and DMSO (2 eq) was slowly added. The precipitated $SnCl_4$-DMSO complex was isolated by filtration. The organic phase was washed with a sodium bicarbonate saturated solution (300 mL) and the organic phases were separated, dried over sodium sulfate and concentrated under low pressure up to a viscous residue. The residue was added with methanol (1500 mL) and a 30% solution of sodium methoxide in methanol (0.4 eq) was added to the resultant solution. The solution was kept under stirring at room temperature for 12 hours and the resultant solid was filtered, washed with methanol (200 mL) and dried. 17 g of azacytidine with a purity of 98.8% (determined by HPLC) and a tin content lower than 200 ppm was obtained.

EXAMPLE 7

Preparation of Azacytidine

To a trimethylsilyl derivative of 5-azacytosine (160 g) dissolved in methylene chloride (800 mL) 1,2,3,5-tetra-O-acetyl-β-D-ribofuranose (1.0 eq) were added and the solution was brought to a temperature of from 0° C. to 10° C. $SnCl_4$ (1.2 eq) was added to the solution and the temperature was left raise up to the room value. At the and of the reaction, the mixture was cooled up to a temperature of from 0° C. to 20° C. and DMSO (2 eq) was slowly added. The precipitated $SnCl_4$-DMSO complex was isolated by filtration, Sodium bicarbonate (4 eq) was added to the organic phase and the mixture was kept under stirring for 1 hour. The solid was removed by filtration and the organic phase was washed with cold water (1000 mL). The organic phases were separated, dried over sodium sulfate and the solvent removed by distillation under low pressure to give a viscous residue. The resultant residue was added with methanol (3 L) and a 30% solution of sodium methoxide in methanol (0.2 eq) was added to the resultant solution.

The solution was kept under stirring at room temperature for 12 hours and the resultant solid was filtered, washed with methanol (300 mL) and dried. 50 g of azacytidine with a purity of 98,8% (determined by HPLC) and a tin content lower than 200 ppm was obtained.

EXAMPLE 8

Preparation of Decitabine

To a trimethylsilyl derivative of 5-azacytosine (6.9 g) dissolved in methylene chloride (34 mL) 1-chloro-3,5-di(4-chlorobenzoyl)-2-deoxy-D-ribose (125 eq) were added and the solution was brought to a temperature of from 0° C. to 10° C. $SnCl_4$ (0.8 eq) was added to the solution and the temperature was left raise up to the room value. At the end of the reaction, the mixture was cooled up to a temperature of from 0° C. to 20° C. and DMSO (4 eq) was slowly added. The precipitated $SnCl_4$-DMSO complex was isolated by filtration. Sodium bicarbonate (4 eq) was added to the organic phase and the mixture was kept under stirring for 1 hour. The solid was removed by filtration and the organic phase was washed with cold water. The organic phases were separated, dried over sodium sulfate and the solvent was removed by distillation under low pressure to give a viscous residue. The residue was added with methanol (70 mL) and a 30% solution of sodium methoxide in methanol (0.2 eq) was added to the resultant solution. The solution was kept under stirring at room temperature for 12 hours and the resultant solid was filtered, washed with methanol (300 mL) and dried. 2.8 g of decitabine with a purity of 98.8% (determined by HPLC) and a tin content lower than 200 ppm was obtained.

EXAMPLE 9

Preparation of Decitabine

To a trimethylsilyl derivative of 5-azacytosine (6.9 g) dissolved in methylene chloride (34 mL) 1-chloro-3,5-di(4-chlorobenzoyl)-2-deoxy-D-ribose (1.25 eq) were added and the solution was brought to a temperature of from 0° C. to 10° C. $SnCl_4$ (0.8 eq) was added to the solution and the temperature was left raise up to the room value. At the end of the reaction, the mixture was cooled up to a temperature of from 0° C. to 20° C. and DMSO (2 eq) was slowly added. The precipitated $SnCl_4$-DMSO complex was isolated by filtration. Sodium bicarbonate (4 eq) was added to the organic phase and the mixture was kept under stirring for 1 hour. The solid was removed by filtration and the organic phase was washed with cold water. The organic phases were separated, dried over sodium sulfate and the solvent was removed by distillation under low pressure to give a viscous residue. The residue was added with methanol (70 mL) and a 30% solution of sodium methoxide in methanol (0.2 eq) was added to the resultant solution. The solution was kept under stirring at room temperature for 12 hours and the resultant solid was filtered, washed with methanol (300 mL) and dried. 2.5 g of decitabine with a purity of 98.8% (determined by HPLC) and a tin content lower than 200 ppm was obtained.

What is claimed is:

1. A process for preparation of a nucleoside, a derivative of a nucleoside, or an analogue of a nucleoside, comprising:
    coupling a suitably protected nitrogenous purine or pyrimidine base, a derivative or analogue thereof with a suitably protected sugar in a reaction mixture containing $SnCl_4$, and
    removing $SnCl_4$ is removed from the reaction mixture by adding DMSO directly into the reaction mixture and subsequently filtering a resultant $SnCl_4$-DMSO complex.

2. A process according to claim 1 wherein DMSO is added in an amount of from 2 equivalents to 4 equivalents with respect to $SnCl_4$.

3. A process according to claim 1 wherein DMSO is added at a temperature of from 0° C. to 20° C.

4. A process according to claim 3 wherein DMSO is added at a temperature of from 0° C. to 10° C.

5. A process according to claim 1 wherein the reaction mixture further comprises a reaction solvent, and the reaction solvent is selected from the group consisting of dichloromethane, chloroform, dichloroethane, acetone, dioxane, tetrahydrofuran, dimethylformamide, benzene, toluene, carbon disulfide, carbon tetrachloride, tetrachloroethane, chlorobenzene, acetonitrile, ethyl acetate and mixtures thereof.

6. A process according to claim 5 wherein the reaction solvent is dichloromethane.

7. A process according to claim 1 further comprising:
    crystallizing the obtained nucleoside, derivative of the nucleoside, or analogue of the nucleoside in a mixture of DMSO and methanol, optionally in the presence of a base.

8. A process according to claim 7 wherein the crystallization is carried out in a mixture of DMSO/methanol in a ratio of 1:3 w/w in the presence of 0.002-0.008 equivalents of sodium methoxide with respect to the non protected suitable nitrogenous purine or pyrimidine base, derivative or analogue thereof.

9. A process according to claim 1 wherein the starting materials are selected to permit the preparation of azacitidine, decitabine, clofarabine, cladribine, or mizoribine.

10. A process according to claim 9 wherein the starting materials are selected to permit the preparation of azacitidine or decitabine.

* * * * *